United States Patent
Gunn

(10) Patent No.: US 9,901,560 B2
(45) Date of Patent: Feb. 27, 2018

(54) METHODS AND COMPOSITIONS FOR TREATMENT OF ACUTE LUNG INJURY

(71) Applicant: Duke University, Durham, NC (US)

(72) Inventor: Michael D. Gunn, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/379,063

(22) Filed: Dec. 14, 2016

(65) Prior Publication Data

US 2017/0165216 A1 Jun. 15, 2017

Related U.S. Application Data

(60) Provisional application No. 62/267,635, filed on Dec. 15, 2015.

(51) Int. Cl.
*A61K 31/198* (2006.01)
*A61K 9/00* (2006.01)

(52) U.S. Cl.
CPC .......... *A61K 31/198* (2013.01); *A61K 9/0019* (2013.01); *A61K 9/0053* (2013.01)

(58) Field of Classification Search
CPC ... A61K 31/198; A61K 9/0019; A61K 9/0053
See application file for complete search history.

(56) References Cited

PUBLICATIONS

Dugo et al (British Journal of Pharmacology, 2004, 141, 979-987).*
Speyer et al (American Journal of Pathology, vol. 163, No. 6, Dec. 2003, 2319-2328).*
Johnson et al (Journal of Aerosol Medicine and Pulmonary Drug Delivery, 2010, vol. 23, No. 4, 243-252).*
Genovese, et al., Inhibition or Knock Out of Inducible Nitric Oxide Synthase Result in Resistance to Bleomycin-Induced Lung Injury, Respiratory Research, 2005, 6:58, 17 pages.
Singh, et al., Selective Inducible Nitric Oxide Synthase Inhibition Has No Effect on Allergen Challenge in Asthma, Am. J. Respir. Crit. Care Med., 2007, 176:988-993.
Standiford, et al., Therapeutic Targeting of Acute Lung Injury and ARDS, Transl. Res., 2016, 167(1):183-191.

\* cited by examiner

*Primary Examiner* — Sudhakar Katakam
(74) *Attorney, Agent, or Firm* — Quarles & Brady LLP

(57) ABSTRACT

A method of treating acute lung injury (ALI) in a patient suspected of having ALI is disclosed. The method includes administering to the patient a therapeutically effective amount of an inducible nitric oxide synthase (iNOS) inhibitor.

17 Claims, 10 Drawing Sheets

METHODS AND COMPOSITIONS FOR TREATMENT OF ACUTE LUNG INJURY

CROSS-REFERENCE TO RELATED APPLICATIONS

This application claims benefit of U.S. Provisional Patent Application No. 62/267,635, filed Dec. 15, 2015, which is incorporated herein by reference as if set forth in its entirety.

STATEMENT REGARDING FEDERALLY SPONSORED RESEARCH

This invention was made with government support under U01ES017219 awarded by the National Institutes of Health. The government has certain rights in the invention.

SEQUENCE LISTING

Not Applicable

BACKGROUND OF THE INVENTION

1. Field of the Invention

This invention relates to treatments for acute lung injury (ALI).

2. Description of the Related Art

ALI is a common clinical syndrome characterized by lung alveolar injury, disruption of the alveolar capillary barrier, a neutrophilic inflammatory response, and marked pulmonary physical dysfunction as assessed by oxygenation, lung compliance, and airway resistance. ALI is caused by a wide variety of insults including trauma, infection, sepsis, and inhalation or aspiration of toxic substances or chemicals.

In patients who develop ALI, the most common and sever manifestation is respiratory failure. Insults leading to ALI cause disruption of the alveolar capillary barrier and alveolar injury. This results in leakage of fluid into the alveoli and marked thickening and inflammation of the alveolar walls. This, in turn, interferes with the ability of the alveoli to deliver inhaled oxygen to the blood. As a result, ALI patients display sever hypoxemia, which can be observed as low blood oxygen levels, which are often incompatible with normal tissue function.

The current state of the art treatment for ALI is supportive care. ALI patients are typically placed on ventilator support in an ICU setting. In recent years, the only significant advances in the treatment of ALI relate to the specifics of how this ventilator support is provided. There presently exists no pharmacologic agents that reduce the major physiologic cause of ALI, namely, disruption of the alveolar capillary barrier, or that reduce the severity or mortality of ALI.

Inducible (or type 2) nitric oxide synthase (iNOS) is known to be related to inflammation conditions. For example, Dugo et al. "Effects of GW274150, a novel and selective inhibitor of iNOS activity, in acute lung inflammation", *British Journal of Pharmacology*, 141, pp. 979-987 (2004) reports that iNOS inhibitors can be effective in treating various inflammatory diseases. However, no evidence has been presented nor has it been hypothesized that this relation to inflammatory conditions would have any implications for the treatment of ALI.

iNOS is also known to be related to the development of bleomycin-induced lung injury. For example, Genovese et al. "Inhibition or knock out of Inducible nitric oxide synthase result in resistance to bleomycin-induced lung injury" *Respiratory Research*, 6:58 (2005) reports that iNOS plays a role in development of bleomycin-inducted lung injury. However, bleomycin-induced lung injury is a separate and distinct condition from ALI and no evidence has been presented nor has it been hypothesized that knowledge regarding the development and treatment of bleomycin-induced lung injury is related to or predictive of development and treatment of ALI.

Accordingly, a need exists for methods and compositions for the treatment of ALI, particularly for treatment of ALI resulting from inhalation of aspiration of toxic substances, such as chlorine.

SUMMARY OF THE INVENTION

In one aspect, the present disclosure provides a method of treating acute lung injury (ALI) in a patient suspected of having ALI. The method can include administering to the patient a therapeutically effective amount of an inducible nitric oxide synthase (iNOS) inhibitor.

In another aspect, the present disclosure provides a use of an iNOS inhibitor for treatment of ALI.

In yet another aspect, the present disclosure provides a method of treating ALI in a patient suspected of having ALI. The method can include one or more of the following steps: measuring one or more properties in the patient; subsequently, administering to the patient a therapeutically effective amount of an iNOS inhibitor; and subsequently, monitoring the one or more properties in the patient. The one or more properties can be selected from the group consisting of: a ratio of arterial oxygen partial pressure to fractional inspired oxygen ($PaO_2/FiO_2$ ratio) in the patient; an oxygenation index in the patient; an airway resistance in the patient; a peak inspiratory pressure in the patient; a lung dynamic compliance in the patient; an oxygen saturation drop in the patient; a mean airway pressure in the patient before; a lung vascular leakage in the patient; and combinations thereof.

These and other features, aspects, and advantages of the present invention will become better understood upon consideration of the following detailed description, drawings and appended claims.

DETAILED DESCRIPTION OF THE INVENTION

Figure 1:
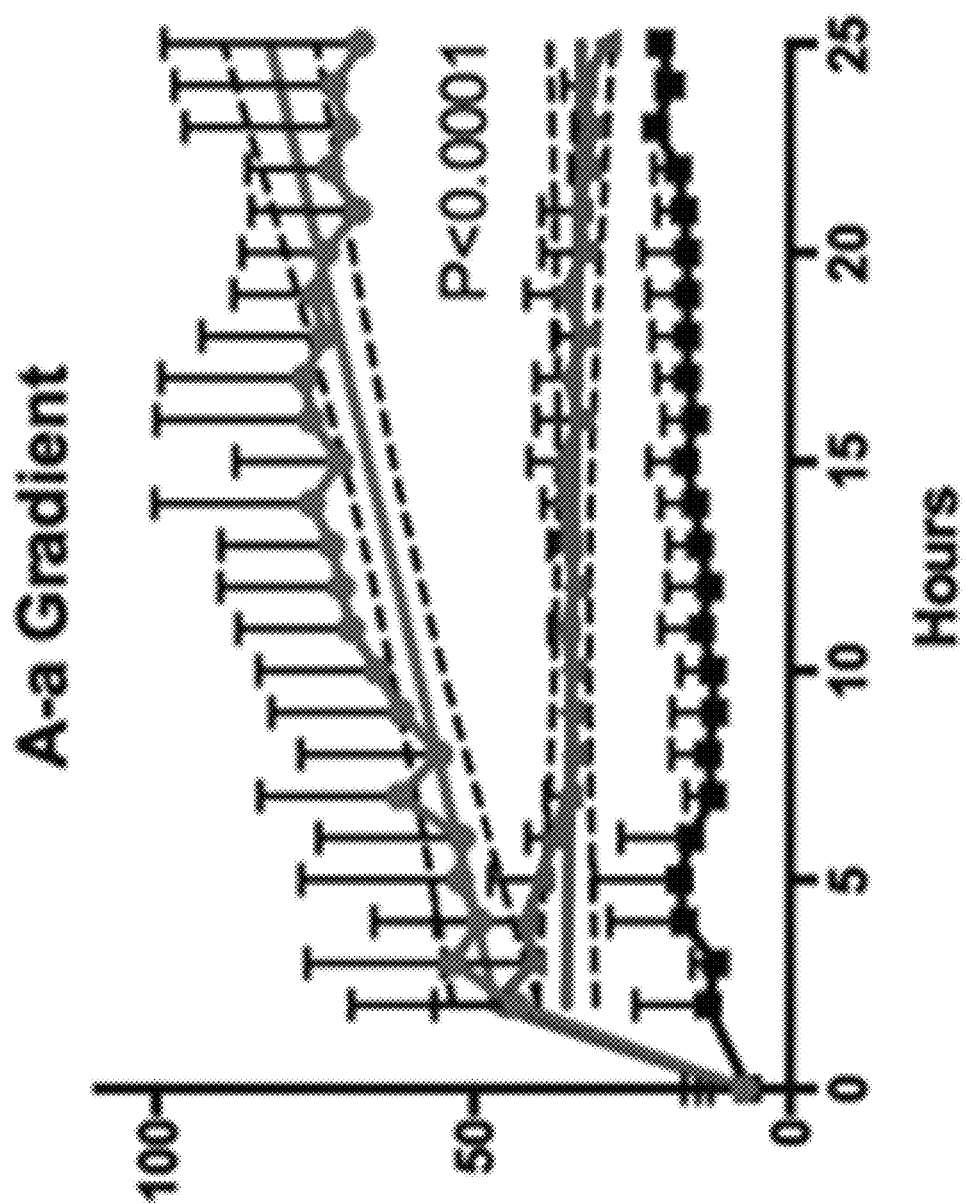
FIG. 1 is a plot of Alveolar–arterial (A–a) $O_2$ gradient for the experiments discussed in Example 1.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

This disclosure relates generally to treatment of ALI. Specifically, this disclosure relates to methods and compositions for treatment of ALI resulting from toxic chemical inhalation.

This disclosure provides a method of treating ALI in a patient suspected of having ALI. The method can include administering to the patient an iNOS inhibitor. The iNOS inhibitor can be administered in a therapeutically effective amount. In certain aspects, the iNOS inhibitor can be (S)-2-amino-(1-iminoethylamino)-5-thioheptanoic acid (GW274150), 2-[2-(4-methoxy-pyridin-2-yl)-ethyl]-3H-imidazo[4,5-b]pyridine (BYK191023), the spiroquinazolone AR-C102222, [3-(2,4-difluorophenyl)-6-[2-[4-(1H-imidazol-1-ylmethyl)phenoxy]ethoxy]-2-phenylpyridine] (PPA250), and (N-[(1,3-benzodioxol-5-yl)methyl]-1-[2-(1H-imidazol-1-yl)pyrimidin-4-yl]-4-(methoxycarbonyl)-piperazine-2-acetamide (BBS-2).

ALI can be induced by a variety of causes. In certain aspects, the ALI can be induced by inhalation or aspiration of a chemical irritant, pneumonia, sepsis, trauma, aspiration of gastric contents, blood transfusions, drug overdose, pancreatitis, burns, near drowning, pulmonary embolus, reperfusion injury, or a combination thereof.

ALI that is induced by inhalation or aspiration of a chemical irritant can be inducted by a variety of chemical irritants. Examples of chemical irritants that can induce ALI that is responsive to the methods and compositions described herein include, but are not limited to, chlorine gas, smoke, phosgene, hydrochloric acid, Acrolein, Ammonia, Aniline, Arsenic trioxide, Arsine, Boron trifluoride, Cyanogen chloride, Hydrogen fluoride, Hydrogen sulfide, Methyl isocyanate, Phosphoro trichloride, Phosphorus trichloride, Sulfur dioxide, Sulfur trioxide, Chlorine dioxide, Bromine, Epichlorohydrin, Fluorine, Hydrazine, Hydrogen selenide, Methyl hydrazine, Benzenethiol, Dimethyl sulfate, Perfluoroisobutene, and combinations thereof.

The administering step can be performed in a variety of ways. In one aspect, the administering can comprise orally administering, intravenous administering, intramuscular administering, subcutaneous administering, administration via aerosol, or a combination thereof.

In aspects where the administering step includes orally administering, the methods can include orally administering the iNOS inhibitor in an amount between 0.01-6.0 mg/Kg, including but not limited to, an amount between 0.01-1.0 mg/Kg, between 1-2 mg/Kg, or between 2-6 mg/Kg.

The doses of the compositions or iNOS inhibitor may be provided as one or several prepackaged units.

The terms "effective amount" or "therapeutically effective amount" refer to an amount sufficient to effect beneficial or desirable biological and/or clinical results.

The duration of the treatment is usually once or twice per day for a period of time that will vary by subject, but will generally last until the condition is essentially controlled. In some embodiments, the duration of treatment may be multiple times per day, twice a day, or once a day, and in some instances may be every other day or once a week depending on the state of the condition.

This disclosure also provides compositions that are tailored for use in treating ALI by way of oral administration. The compositions can include a pharmaceutically acceptable carrier and the iNOS inhibitor in an amount between 0.01-6.0 mg/Kg, including but not limited to, an amount between 0.01-1.0 mg/Kg, between 1-2 mg/Kg, or between 2-6 mg/Kg. Formulations suitable for oral administration include tablets bound with inert carriers and water-based oral solutions, among other formulations understood by those having ordinary skill in the art to be suitable for the oral administration described herein.

Solid dosage forms for oral administration include capsules, tablets, powders, and granules. In such solid dosage forms, the iNOS inhibitor is admixed with at least one inert customary excipient (or carrier). Suitable inert customary excipients are known in the art, such as, for example, but not limited to, sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent.

Tablets may be manufactured with pharmaceutically acceptable excipients such as inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Suitable liquid carrier(s) can be a solvent or dispersion medium including, without limitation, water, ethanol, polyol (e.g., glycerol, propylene glycol, and liquid polyethylene glycol, and the like, or a combination thereof), one or more vegetable oils, or any combination thereof, although additional pharmaceutically-acceptable components may be included.

In aspects where the administering step includes intravenous administering, the methods can include intravenous administering the iNOS inhibitor in an amount between 0.01-6.0 mg/Kg, including but not limited to, an amount between 0.01-1.0 mg/Kg, between 1-2 mg/Kg, or between 2-6 mg/Kg.

This disclosure also provides compositions that are tailored for use in treating ALI by way of intravenous administration. The compositions can include a pharmaceutically acceptable carrier and the iNOS inhibitor in an amount between 0.01-6.0 mg/Kg, including but not limited to, an amount between 0.01-1.0 mg/Kg, between 1-2 mg/Kg, or between 2-6 mg/Kg dissolved in normal saline or an analogous physiologic fluid.

In aspects where the administering step includes intramuscular administering, the methods can include intramuscular administering the iNOS inhibitor in an amount between 0.01-6.0 mg/Kg, including but not limited to, an amount between 0.01-1.0 mg/Kg, between 1-2 mg/Kg, or between 2-6 mg/Kg.

This disclosure also provides compositions that are tailored for use in treating ALI by way of intramuscular administration. The compositions can include a pharmaceutically acceptable carrier and the iNOS inhibitor in an amount between 0.01-6.0 mg/Kg, including but not limited to, an amount between 0.01-1.0 mg/Kg, between 1-2 mg/Kg, or between 2-6 mg/Kg dissolved in normal saline or an analogous physiologic fluid.

In one embodiment of the invention, the iNOS inhibitor or compositions of the invention are administered directly to the lungs of the subject by any suitable means, but are preferably administered by administering an aerosol suspension of respirable particles comprised of the iNOS inhibitor, which the subject inhales. The iNOS inhibitor can be aerosolized in a variety of forms, such as, but not limited to, dry powder inhalants, metered dose inhalants, or liquid/liquid suspensions. The respirable particles may be liquid or solid.

In aspects where the administering step includes aerosol administering, the methods can include aerosol administering the iNOS inhibitor in an amount between 0.01-6.0 mg/Kg, including but not limited to, an amount between 0.01-1.0 mg/Kg, between 1-2 mg/Kg, or between 2-6 mg/Kg.

Solid or liquid particulate forms of the iNOS inhibitor prepared for practicing the present invention should include particles of respirable size: that is, particles of a size sufficiently small to pass through the mouth and larynx upon inhalation and into the bronchi and alveoli of the lungs of a subject. In general, particles ranging from about 1 to 10 microns in size are within the respirable range. Particles of non-respirable size which are included in the aerosol tend to be deposited in the throat and swallowed, and the quantity of non-respirable particles in the aerosol is preferably minimized. The particulate composition may optionally be combined with a carrier to aid in dispersion or transport. A suitable carrier such as a sugar (i.e., lactose, sucrose, trehalose, mannitol) may be blended with the iNOS inhibitor(s) in any suitable ratio (e.g., a 1 to 1 ratio by weight).

Suitably, the compositions may be formulated into aerosols to be administered by inhalation. Aerosols of liquid particles comprising the iNOS inhibitor may be produced by any suitable means, such as with a pressure-driven aerosol nebulizer or an ultrasonic nebulizer. See, e.g., U.S. Pat. No. 4,501,729, incorporated by reference in its entirety.

Nebulizers are commercially available devices known in the art which transform solutions or suspensions of the active ingredient into a therapeutic aerosol mist either by means of acceleration of compressed gas, typically air or oxygen, through a narrow orifice or by means of ultrasonic agitation. Several types of nebulizers are available, including, for example, jet nebulizers, ultrasonic nebulizers, vibrating mesh nebulizers.

Aerosols of solid particles comprising the iNOS inhibitor(s) may likewise be produced with any solid particulate medication aerosol generator. Aerosol generators for administering solid particulate medicaments to a subject are known in the art, for example, generate a volume of aerosol containing a predetermined metered dose of a medicament at a rate suitable for human administration. For example, a solid particulate aerosol generator may be, but not limited to, an insufflator or a metered dose inhaler. Suitable compositions for administration by insufflation include finely comminuted powders which may be delivered by means of an insufflator or taken into the nasal cavity in the manner of a snuff.

The powder employed in the insufflator may consist either solely of the active ingredient or of a powder blend comprising the active ingredient, a suitable powder diluent, such as lactose, and an optional surfactant. The iNOS inhibitor typically comprises from 0.1 to 100 w/w of the composition.

Suitable propellants include certain chlorofluorocarbon compounds, for example, dichlorodifluoromethane, trichlorofluoromethane, dichlorotetrafluoroethane and mixtures thereof. The composition may additionally contain one or more co-solvents, for example, ethanol, surfactants, such as oleic acid or sorbitan trioleate, antioxidants and suitable flavoring agents.

The method can further include measuring, monitoring, assessing, or in any other way determining one or more properties in the patient. These properties can be measured prior to the administering and at various time points after the administering. The changes in the properties can be an indication of the efficacy of the treatment. The one or more properties can be selected from the group consisting of: a ratio of arterial oxygen partial pressure to fractional inspired oxygen ($PaO_2/FiO_2$ ratio) in the patient; an oxygenation index in the patient; an airway resistance in the patient; a peak inspiratory pressure in the patient; a lung dynamic compliance in the patient; an oxygen saturation drop in the patient; a mean airway pressure in the patient before; a lung vascular leakage in the patient; other clinical measures of respiratory function; and combinations thereof.

The Alveolar-arterial gradient (A-aO$_2$ or A-a gradient), is a measure of the difference between the alveolar concentration (A) of oxygen and the arterial (a) concentration of oxygen. The equation for calculating the A-a gradient is: Aa Gradient=P$_A$O$_2$-P$_a$O$_2$, where P$_A$O$_2$=alveolar PO$_2$ (calculated from the alveolar gas equation), P$_A$O$_2$=FiO$_2$ (P$_{atm}$-P$_{H2O}$)-P$_a$CO$_2$/0.8, where FiO$_2$=the fraction of inspired oxygen, P$_{H2O}$=the partial pressure of water in the air, P$_a$CO$_2$=partial pressure of arterial carbon dioxide, measured directly from a blood gas, and P$_a$O$_2$=arterial PO$_2$, measured directly from a blood gas.

The P$_a$O$_2$/FiO$_2$ ratio is the ratio of arterial oxygen partial pressure, measured directly from a blood gas, to fractional inspired oxygen.

The oxygenation index is calculated using the formula oxygenation index=(FiO$_2$×M$_{Paw}$)/P$_a$O$_2$, where FiO$_2$=the fraction of inspired oxygen, M$_{Paw}$=Mean airway pressure, and P$_a$O$_2$=arterial PO$_2$, measured directly from a blood gas.

Mean airway pressure is the mean pressure applied during positive-pressure mechanical ventilation. This measurement is provided in real time by intensive care unit ventilators.

Airway resistance is the resistance of the respiratory tract to airflow during inspiration and expiration. This measurement is provided in real time by intensive care unit ventilators.

Peak inspiratory pressure is the highest level of pressure applied to the lungs during the inhalation phase of mechanical ventilation. This measurement is provided in real time by intensive care unit ventilators.

Lung compliance is a measure of the lung's ability to stretch and expand. Dynamic compliance represents lung compliance during periods of gas flow, such as during active inspiration. This measurement is provided in real time by intensive care unit ventilators.

Oxygen saturation is a term referring to the fraction of oxygen-saturated hemoglobin relative to total hemoglobin (unsaturated+saturated) in the blood. Oxygen saturation is measured in real time using a pulse oximeter.

Lung vascular leakage is an inappropriate movement of fluid from the blood into the lung alveoli caused by injury to lung cells and membranes. Lung vascular leakage can be measured by injecting a labeled high-molecular weight substance, such as FITC-Dextran, into the blood, waiting a short period of time, such a one hour, then sampling the contents of the lung alveoli using bronchoalveolar lavage (BAL). A high concentration of the labeled substance in the recovered BAL fluid suggests increased lung vascular leakage.

Example 1

The efficacy of a iNOS inhibitor in reducing ALI has been demonstrated in a preclinical model. In the model, ~30 kg Yorkshire pigs (*Sus scrofa domesticus*) were sedated, intubated, placed on a ventilator, and instrumented with arterial, pulmonary artery, and bladder catheters. Baseline hemodynamic, respiratory, and metabolic parameters were observed. The pigs were then exposed to 240 ppm chlorine gas via an endotracheal tube for 1 hour. After exposure, the pigs remained sedated and ventilated and all measurements were repeated hourly until the end of the study. One hour after the end of chlorine exposure, pigs were treated with either 200 mg of GW274150 or vehicle via intramuscular injection. 22 hours after exposure, the pigs were injected intravenously with fluorescein isothiocyanate-dextran to measure lung vascular leakage. One hour later (23 hours after exposure), the pigs were subjected to bronchoscopy and bronchoalveolar lavage (BAL). The pigs were then euthanized and lung tissues were obtained for pathologic analysis. Pigs exposed to chlorine gas in this manner displayed all major features of human chlorine-induced ALI including histological evidence of tissue injury, alteration of the alveolar capillary barrier, a neutrophilic inflammatory response, and marked pulmonary physiological dysfunction.

Relative to vehicle treated pigs, pigs treated with GW274150 displayed improved outcomes as illustrated in FIGS. 1-9. In FIGS. 1-8, the black plot corresponds to pigs that were exposed to filtered air, the red plot corresponds to pigs that were exposed to chlorine followed by placebo, and the blue plot corresponds to pigs that were exposed to chlorine followed by treatment with GW274150. Statistical significance was determined by performing linear regression of all data points obtained after drug or placebo administration and comparing the slopes of the placebo and GW274150 treatment groups. Dotted lines denote 99% confidence intervals.

Figure 2:
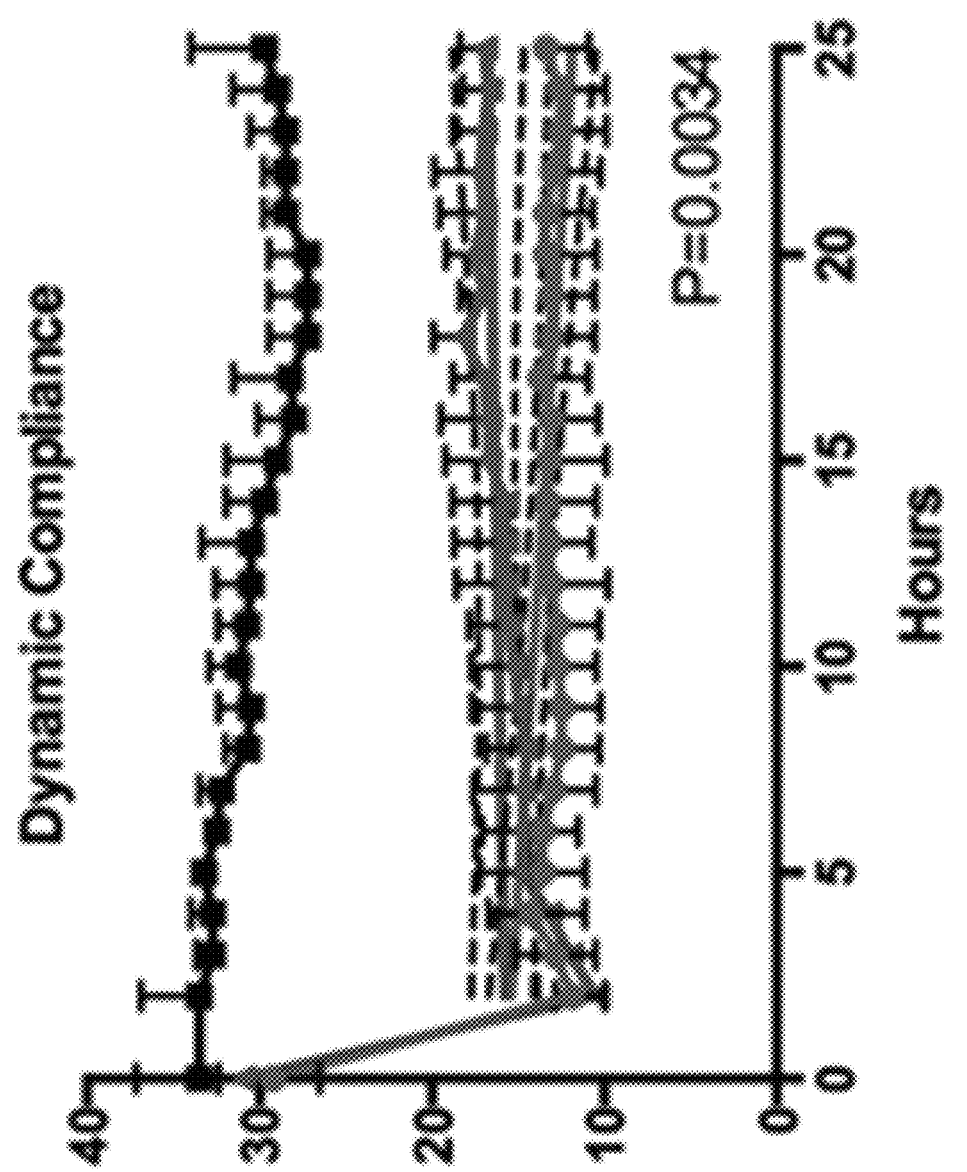
FIG. 2 is a plot of arterial oxygen partial pressure to fractional inspired oxygen ($PaO_2/FiO_2$ ratio) for the experiments discussed in Example 1.
Figure 3:
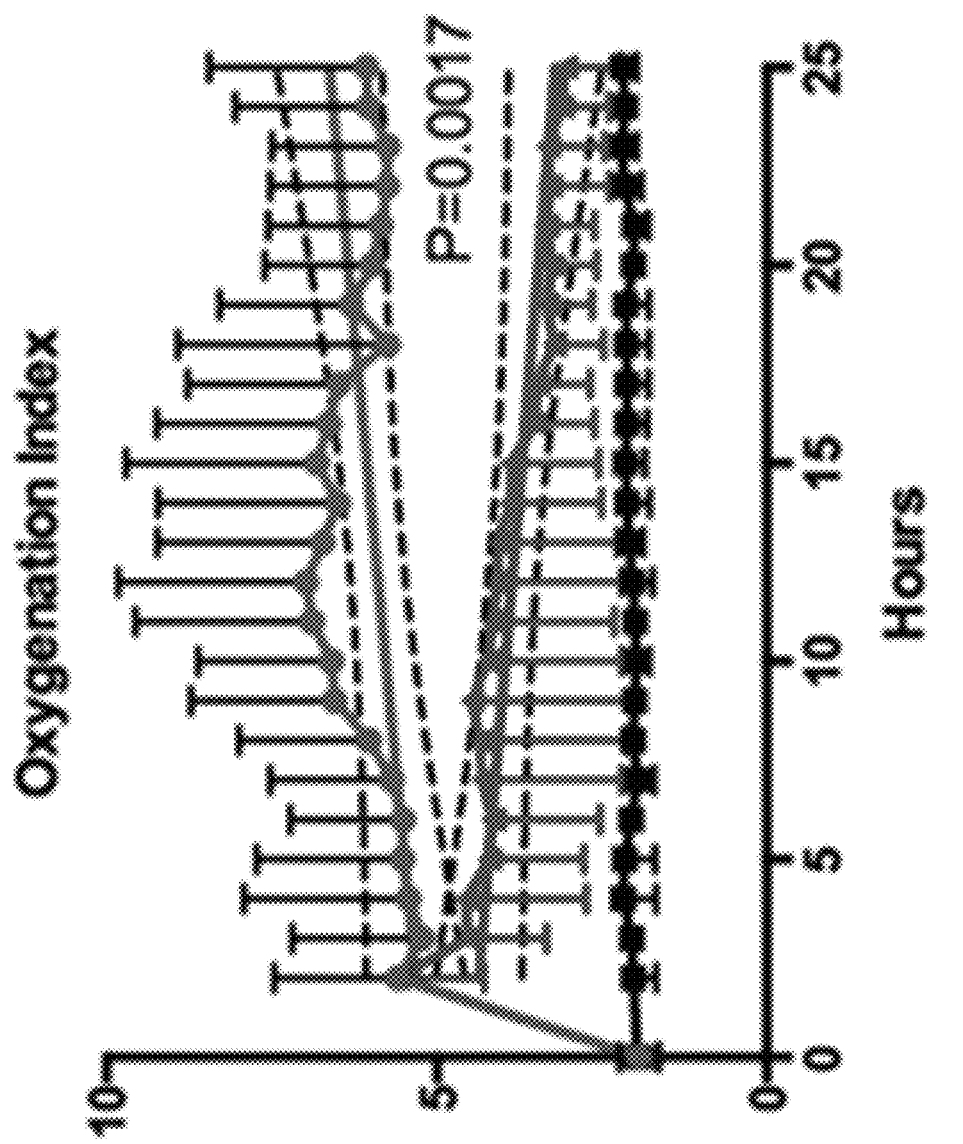
FIG. 3 is a plot of Oxygenation index for the experiments discussed in Example 1.
Figure 4:
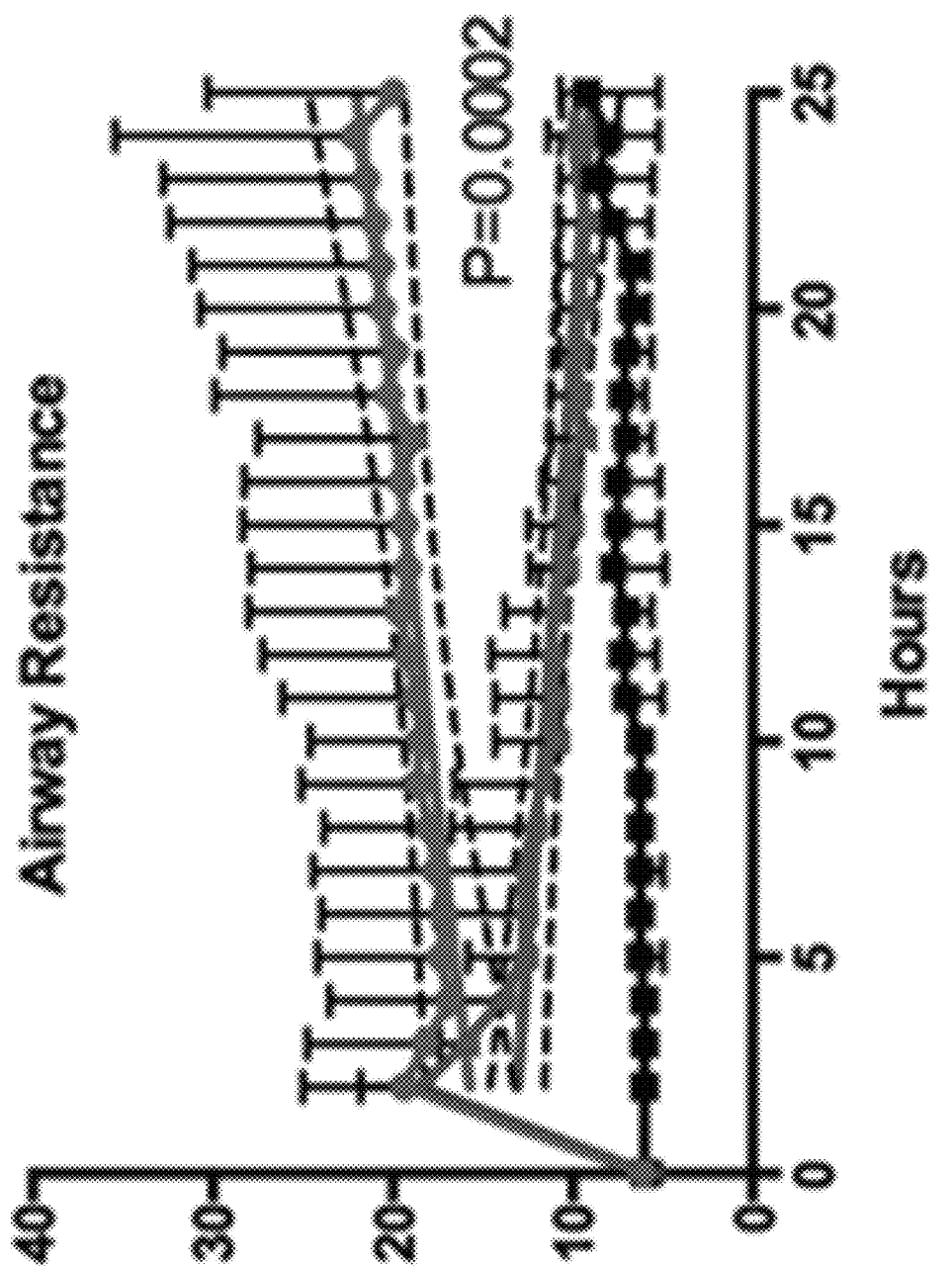
FIG. 4 is a plot of Airway Resistance for the experiments discussed in Example 1.
Figure 5:
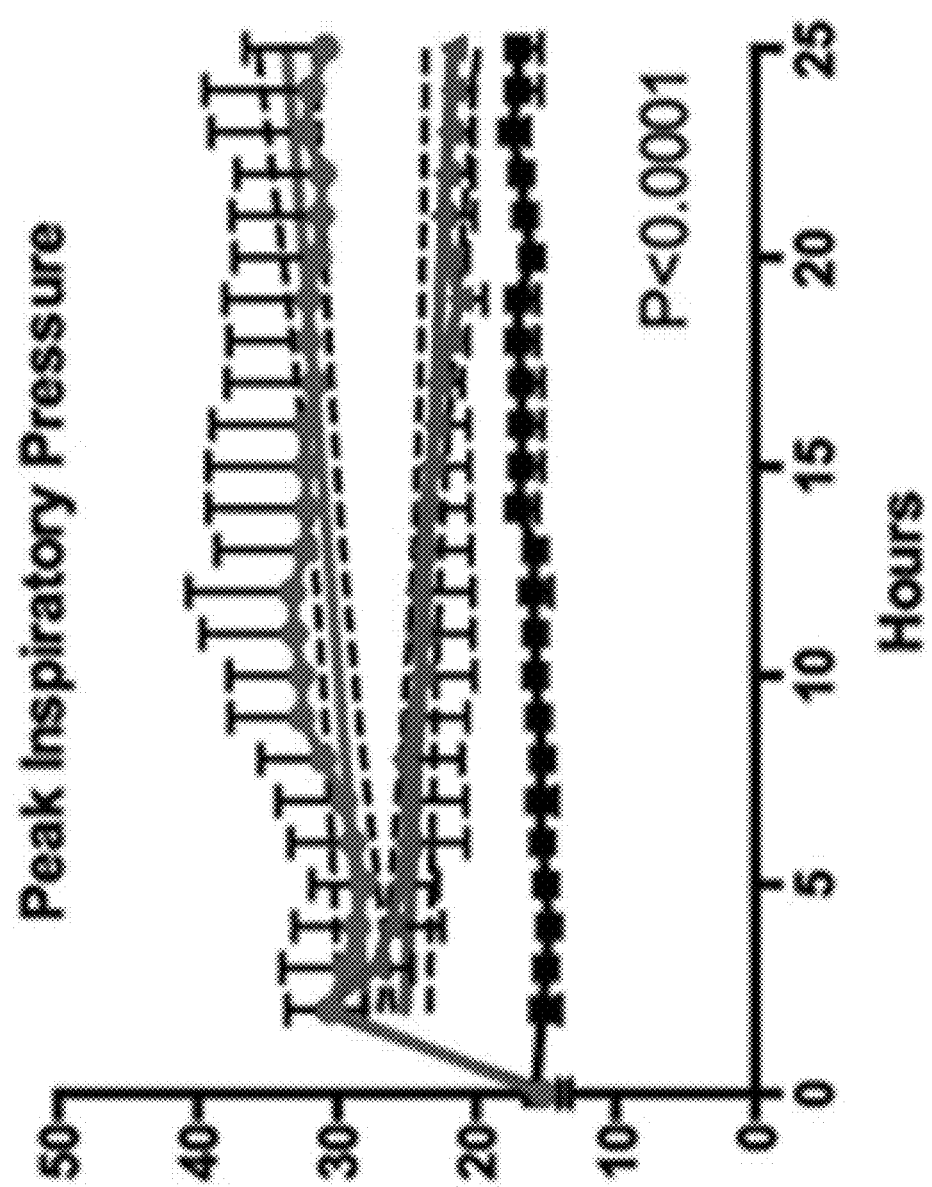
FIG. 5 is a plot of Peak Inspiratory Pressures for the experiments discussed in Example 1.
Figure 6:
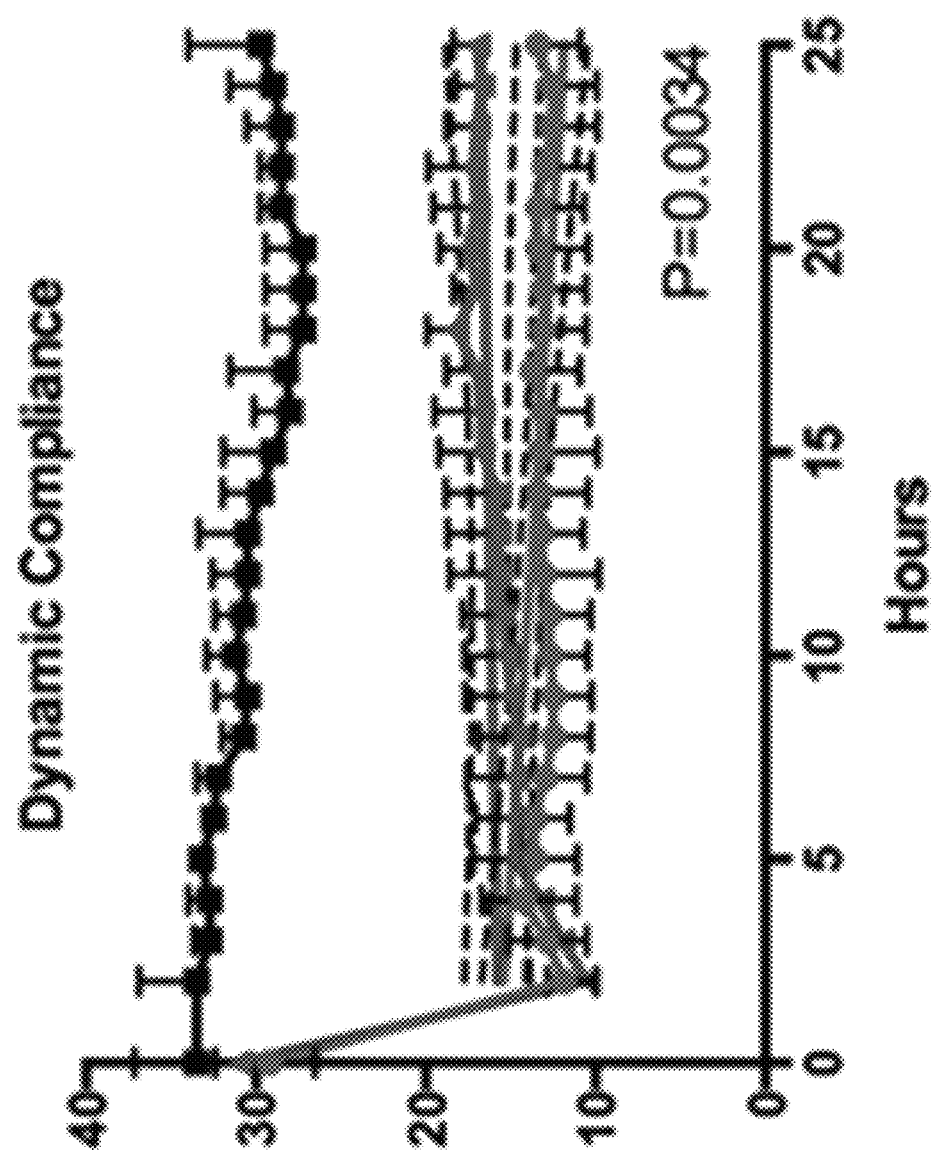
FIG. 6 is a plot of Lung Dynamic Compliance for the experiments discussed in Example 1.
Figure 7:
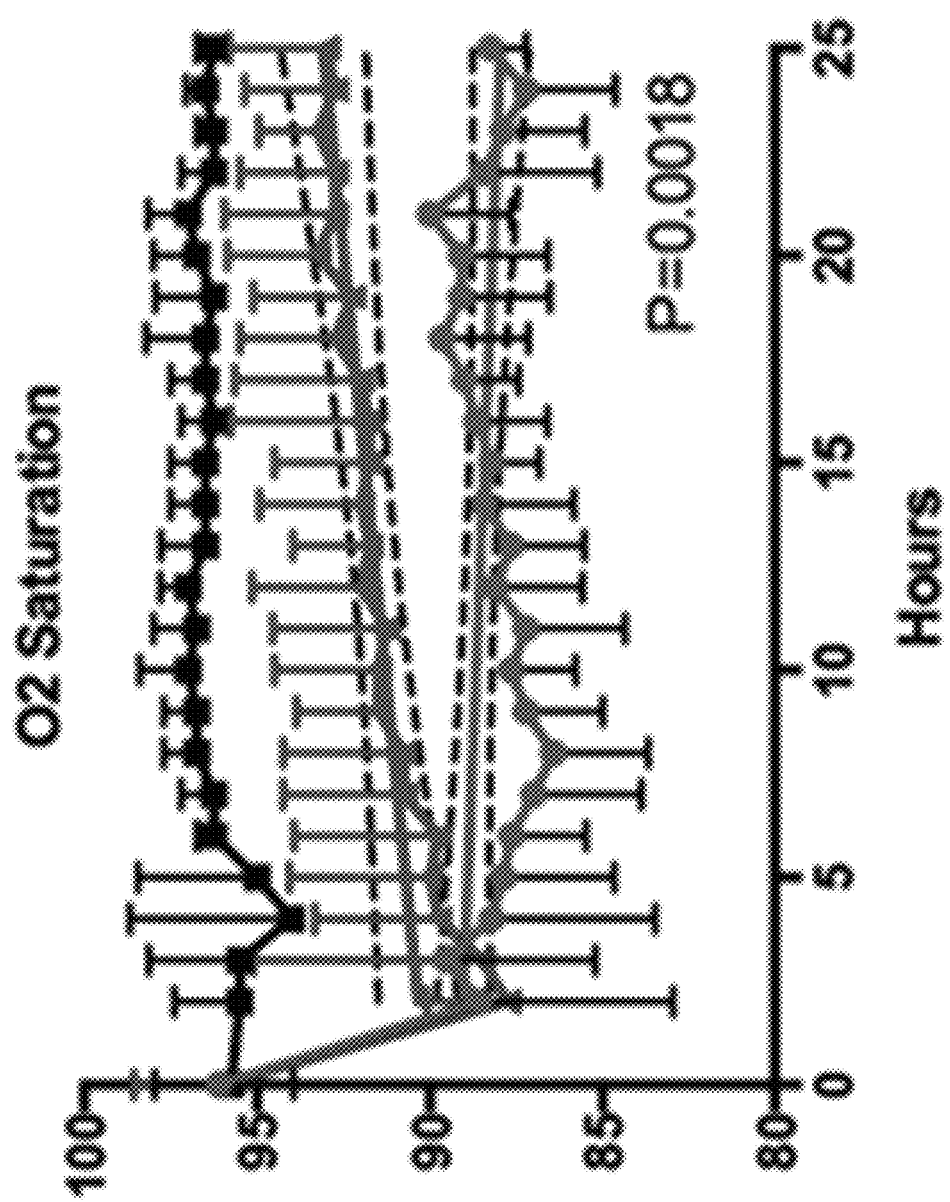
FIG. 7 is a plot of $O_2$ Saturation for the experiments discussed in Example 1.
Figure 8:
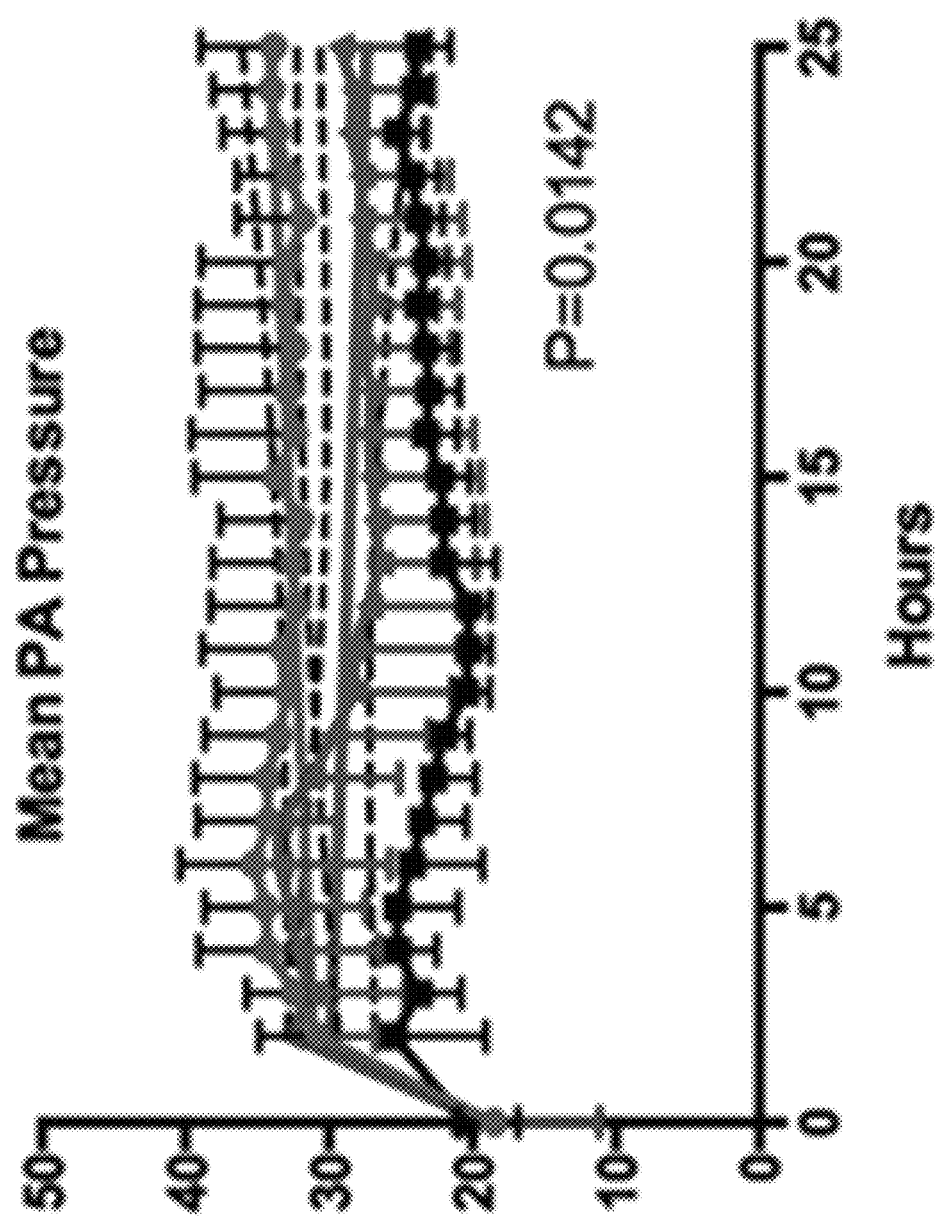
FIG. 8 is a plot of Mean Airway Pressure for the experiments discussed in Example 1.
Figure 9:
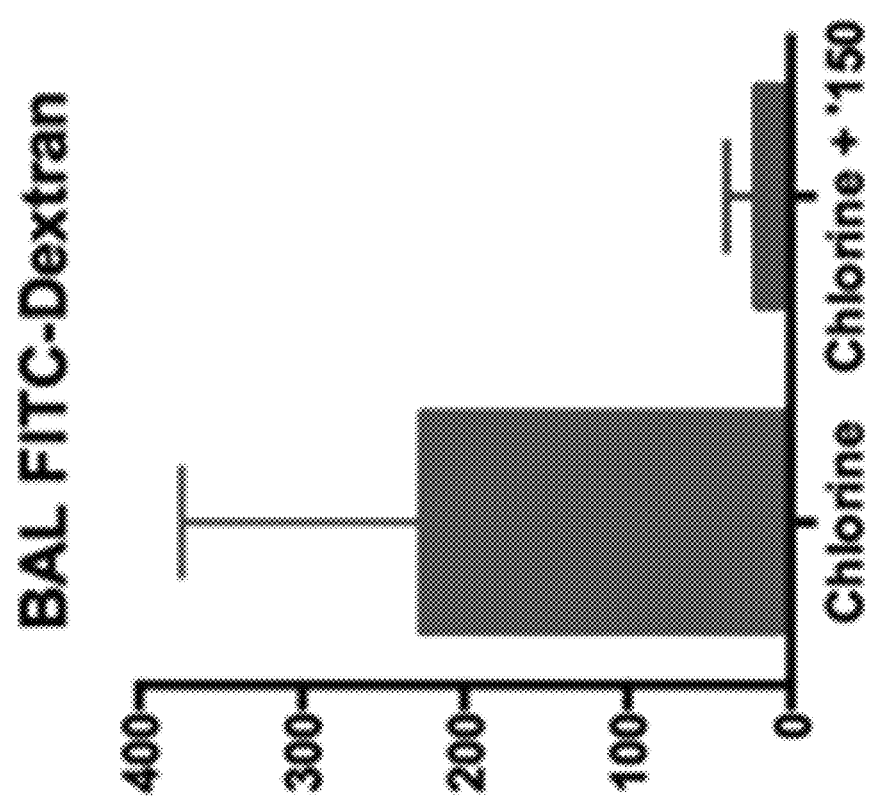
FIG. 9 is a plot of lung vascular leakage for the experiments discussed in Example 1.

As illustrated in FIG. 1, GW274150-treated pigs displayed a 55% decrease in the Alveolar-arterial (A-a) O$_2$ gradient on average 12-24 hours post exposure, when compared with vehicle-treated pigs. As illustrated in FIG. 2, GW274150-treated pigs displayed a 41% increase in a ratio of arterial oxygen partial pressure to fractional inspired oxygen (PaO$_2$/FiO$_2$ ratio) on average 12-24 hours post exposure, when compared with vehicle-treated pigs. As illustrated in FIG. 3, GW274150-treated pigs displayed a 60% decrease in Oxygenation index on average 12-24 hours post exposure, when compared with vehicle-treated pigs. As illustrated in FIG. 4, GW274150-treated pigs displayed a 69% decrease in Airway Resistance on average 12-24 hours post exposure, when compared with vehicle-treated pigs. As illustrated in FIG. 5, GW274150-treated pigs displayed a 42% decrease in Peak Inspiratory Pressures on average 12-24 hours post exposure, when compared with vehicle-treated pigs. As illustrated in FIG. 6, GW274150-treated pigs displayed a 33% increase in Lung Dynamic Compliance on average 12-24 hours post exposure, when compared with vehicle-treated pigs. As illustrated in FIG. 7, GW274150-treated pigs displayed a 49% decrease in O$_2$ Saturation drop on average 12-24 hours post exposure, when compared with vehicle-treated pigs. As illustrated in FIG. 8, GW274150-treated pigs displayed a 57% decrease in Mean Airway Pressure on average 12-24 hours post exposure, when compared with vehicle-treated pigs. As illustrated in FIG. 9, GW274150-treated pigs displayed a at 24 hours post exposure as measured by FITC-dextran extravasion from blood to BAL fluid, when compared with vehicle-treated pigs.

The efficacy of a iNOS inhibitor in reducing chlorine-induced mortality has also been demonstrated in a preclinical model. In this model, rabbits are intubated, exposed to chlorine gas at the LD$_{50}$ dose (150 ppm for 20 minutes), then extubated and followed for the next 24 hours. Rabbits were treated with vehicle or GW274150 1 hour after the end of chlorine exposure.

Figure 10B:
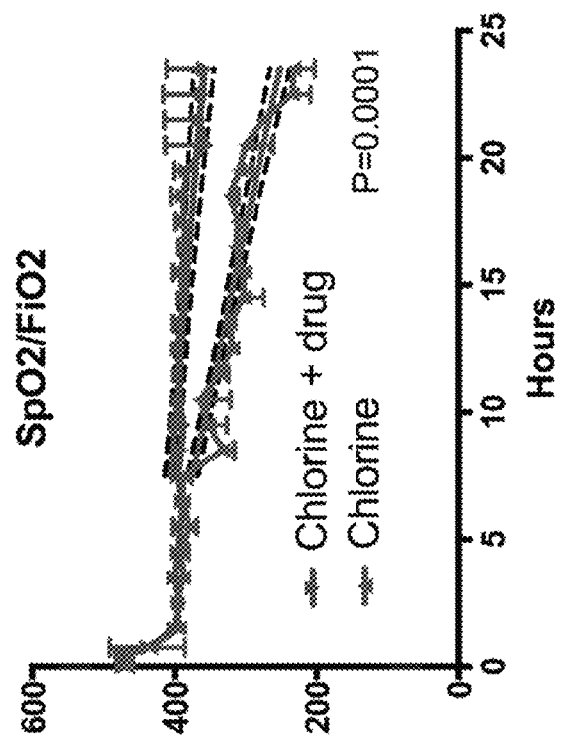
FIG. 10B is a plot of SpO2/FiO2 ratios over time in the rabbits that survived 24 hours in FIG. 10A.
Figure 10A:
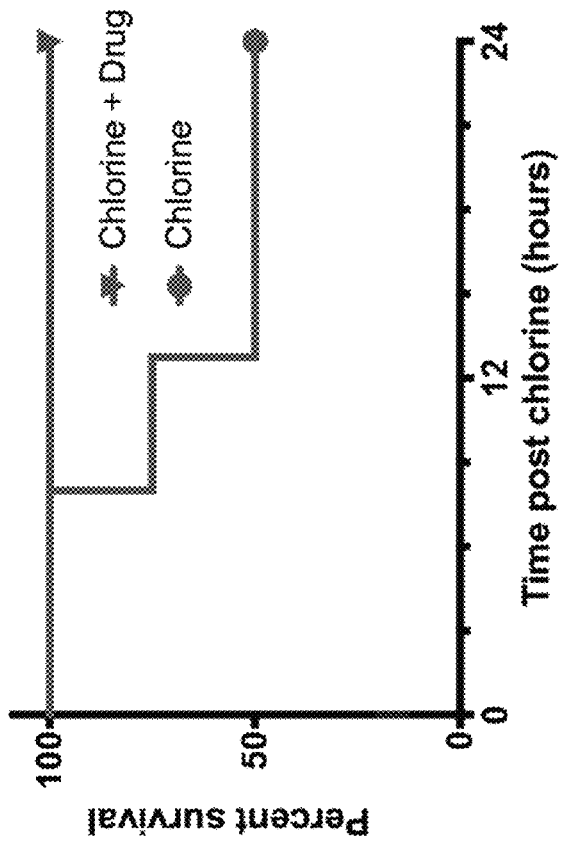
FIG. 10A is a plot of survival in chlorine-exposed rabbits in the presence and absence of iNOS inhibition.

As illustrated in FIG. 10A, GW274150-treated rabbits displayed complete protection from chlorine-induced mortality. In addition, as illustrated in FIG. 10B, those vehicle-treated rabbits that survived displayed significantly more severe ALI, as measured by SpO2/FiO2 ratios, than GW274150-treated rabbits.

These results demonstrated the efficacy of a iNOS inhibitor in attenuating the development of ALI in models that are representative of chemical-induced ALI in humans. This attenuation of ALI is sufficient to prevent chlorine-induced mortality after what would otherwise be a lethal dose of chlorine gas.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method of treating acute lung injury (ALI) in a patient suspected of having ALI, the method comprising:
  administering to the patient a therapeutically effective amount of an inducible nitric oxide synthase (iNOS) inhibitor, wherein the iNOS inhibitor is (S)-2-amino-(1-iminoethylamino)-5-thioheptanoic acid (GW274150).

2. The method of claim 1, wherein the ALI is induced by inhalation or aspiration of a chemical irritant.

3. The method of claim 2, wherein the chemical irritant is selected from a group consisting of chlorine gas, smoke, phosgene, and combinations thereof.

4. The method of claim 1, wherein the administering comprises orally administering, intravenous administering, intramuscular administering or aerosol administering.

5. The method of claim 4, wherein the administering comprises orally administering the iNOS inhibitor in an amount between 0.1 mg/Kg to 6.0 mg/Kg.

6. The method of claim 4, wherein the administering comprises intravenous administering the iNOS inhibitor in an amount between 0.1 mg/Kg to 6.0 mg/Kg.

7. The method of claim 4, wherein the administering comprises intramuscular administering the iNOS inhibitor in an amount between 0.1 mg/Kg to 6.0 mg/Kg.

8. The method of claim 1, the method further comprising one or more of the following steps:
  monitoring an alveolar-arterial oxygen gradient in the patient before or after the administering;
  monitoring a ratio of arterial oxygen partial pressure to fractional inspired oxygen ($PaO_2/FiO_2$ ratio) in the patient before or after the administering;
  monitoring an oxygenation index in the patient before or after the administering;
  monitoring an airway resistance in the patient before or after the administering;
  monitoring a peak inspiratory pressure in the patient before or after the administering;
  monitoring a lung dynamic compliance in the patient before or after the administering;
  monitoring an oxygen saturation drop in the patient before or after the administering;
  monitoring a mean airway pressure in the patient before or after the administering; or
  monitoring a lung vascular leakage in the patient before or after the administering.

9. A method of treating acute lung injury (ALI) in a patient suspected of having ALI, the method comprising:
  a) measuring one or more properties in the patient, the one or more properties selected from the group consisting of:
    a ratio of arterial oxygen partial pressure to fractional inspired oxygen ($PaO_2/FiO_2$ ratio) in the patient;
    an oxygenation index in the patient;
    an airway resistance in the patient;
    a peak inspiratory pressure in the patient;
    a lung dynamic compliance in the patient;
    an oxygen saturation drop in the patient;
    a mean airway pressure in the patient before;
    a lung vascular leakage in the patient; and
    combinations thereof;
  b) subsequent to step a), administering to the patient a therapeutically effective amount of an inducible nitric oxide synthase (iNOS) inhibitor, wherein the iNOS inhibitor is (S)-2-amino-(1-iminoethylamino)-5-thioheptanoic acid (GW274150); and
  c) subsequent to step b), monitoring the one or more properties in the patient.

10. The method of claim 9, wherein the ALI is induced by inhalation or aspiration of a chemical irritant.

11. The method of claim 10, wherein the chemical irritant is selected from a group consisting of chlorine gas, smoke, phosgene, and combinations thereof.

12. The method of claim 9, wherein the administering comprises orally administering, intravenous administering, intramuscular administering or aerosol administering.

13. The method of claim 12, wherein the administering comprises orally administering the iNOS inhibitor in an amount between 0.1 mg/Kg to 6.0 mg/Kg.

14. The method of claim 9, wherein the administering comprises intravenous administering.

15. The method of claim 14, wherein the administering comprises intravenous administering the iNOS inhibitor in an amount between 0.1 mg/Kg to 6.0 mg/Kg.

16. The method of claim 9, wherein the administering comprises intramuscular administering.

17. The method of claim 16, wherein the administering comprises intramuscular administering the iNOS inhibitor in an amount between 0.1 mg/Kg to 6.0 mg/Kg.

* * * * *